US011158416B1

(12) United States Patent
Sharp

(10) Patent No.: US 11,158,416 B1
(45) Date of Patent: Oct. 26, 2021

(54) METHODS AND SYSTEMS FOR TREATMENT OF FEEDING DISORDERS

(71) Applicant: Children's Healthcare of Atlanta, Inc., Atlanta, GA (US)

(72) Inventor: William G. Sharp, Decatur, GA (US)

(73) Assignee: Children's Healthcare of Atlanta, Inc., Atlanta, GA (US)

( * ) Notice: Subject to any disclaimer, the term of this patent is extended or adjusted under 35 U.S.C. 154(b) by 575 days.

(21) Appl. No.: 15/943,209

(22) Filed: Apr. 2, 2018

Related U.S. Application Data

(60) Provisional application No. 62/491,538, filed on Apr. 28, 2017, provisional application No. 62/479,855, filed on Mar. 31, 2017.

(51) Int. Cl.
G16H 20/60 (2018.01)
G16H 50/70 (2018.01)
G16H 50/50 (2018.01)

(52) U.S. Cl.
CPC ............. *G16H 20/60* (2018.01); *G16H 50/70* (2018.01); *G16H 50/50* (2018.01)

(58) Field of Classification Search
CPC ........ G16H 20/60; G16H 50/70; G16H 20/70; A61B 5/4833
See application file for complete search history.

(56) References Cited

U.S. PATENT DOCUMENTS

| 2005/0112534 | A1 | 5/2005 | McCarton et al. | |
| 2007/0244375 | A1 | 10/2007 | Jenkins et al. | |
| 2016/0135738 | A1* | 5/2016 | Bowers | A61B 5/4833 600/301 |

FOREIGN PATENT DOCUMENTS

WO 2016167975 A1 10/2016

OTHER PUBLICATIONS

Laud, et al., Treatment Outcomes for Severe Feeding Problems in Children with Autism Spectrum Disorder, Behavior Modificiation, vol. 33, No. 5, Sep. 2009.
Sharp, et al., Multi-Method Assessment of Feeding Problems Among Children with Autism Spectrum Disorders, Research in Autism Spectrum Disorders, 2012.
Matson, et al., The Treatment of Food Selectivity and Other Feeding Problems in Children with Autism Spectrum Disorders, Research in Autism Spectrum Disorders, 2008.

(Continued)

*Primary Examiner* — Jerry-Daryl Fletcher
(74) *Attorney, Agent, or Firm* — Morris, Manning & Martin, LLP; Daniel E. Sineway, Esq.

(57) ABSTRACT

Methods and systems for treatment of feeding disorders in individuals by a multi-disciplinary team comprising medical, behavioral, nutritional, and oral-motor skill professionals and/or specialists. For example, in one embodiment, a subject may go through treatment that comprises four phases/process: screening, assessment, intervention, and discharge. The screening process may determine the subject's eligibility for the treatment. The assessment process may establish a baseline from which the specific treatment is determined. The intervention process generally implements the treatment through daily "doses" of treatment meal sessions. The discharge process may ensure that the treatment gains made during the intervention phase are carried into the subject's daily life.

12 Claims, 7 Drawing Sheets

EXEMPLARY SYSTEM ARCHITECTURE

(56) References Cited

OTHER PUBLICATIONS

Sharp, et al., A Systematic Review and Meta-Analysis of Intensive Multidisciplinary Intervention for Pediatric Feeding Disorders: How Standard is the Standard of Care?, The Journal of Pediatrics, vol. 181, Feb. 2017.

Romano, et al., Current Topics in the Diagnosis and Management of the Pediatric Non Organic Feeding Disorders (NOFEDs), Clinical Nutrition, 2014.

* cited by examiner

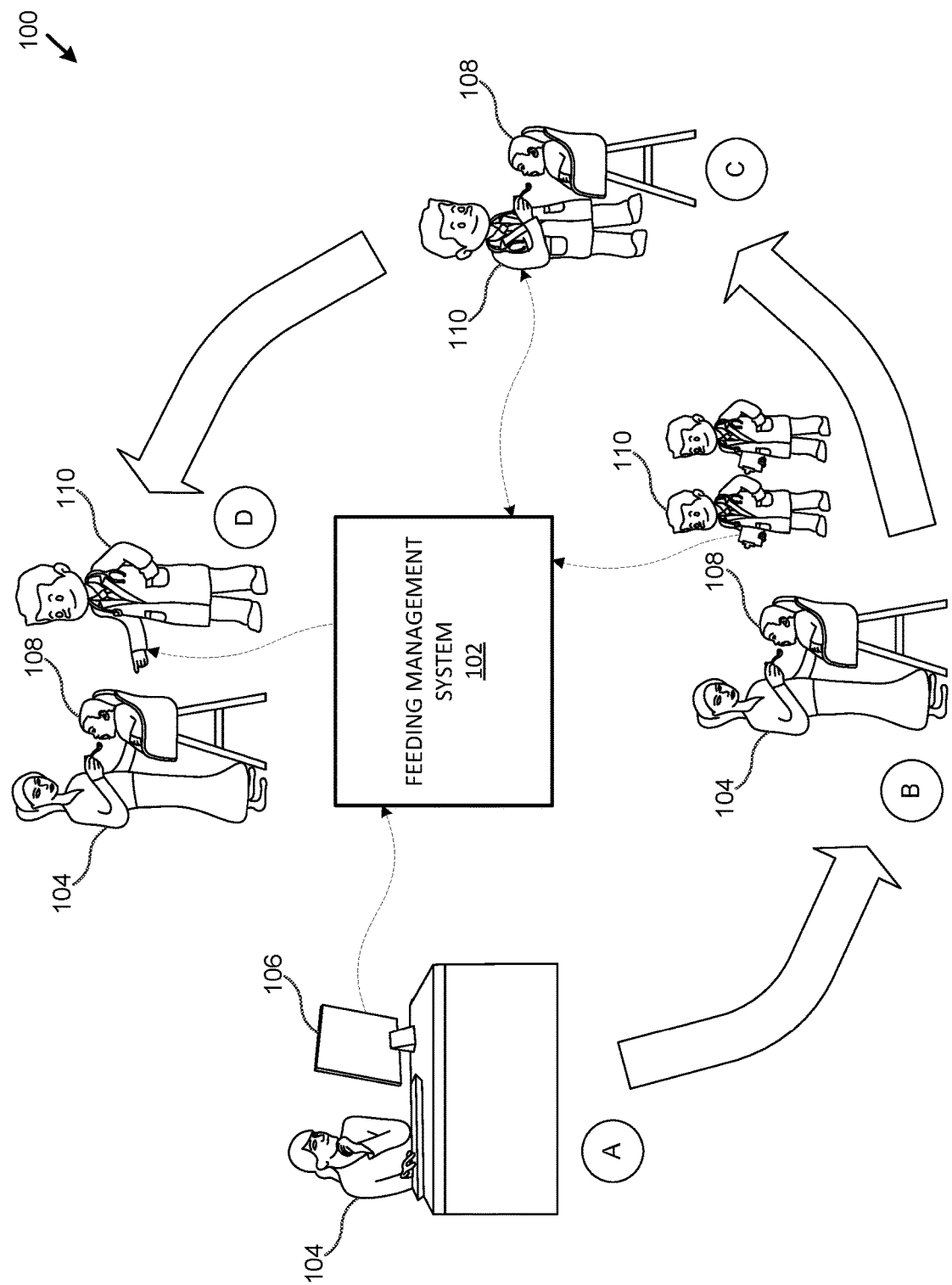
FIG 1: EXEMPLARY SYSTEM OVERVIEW

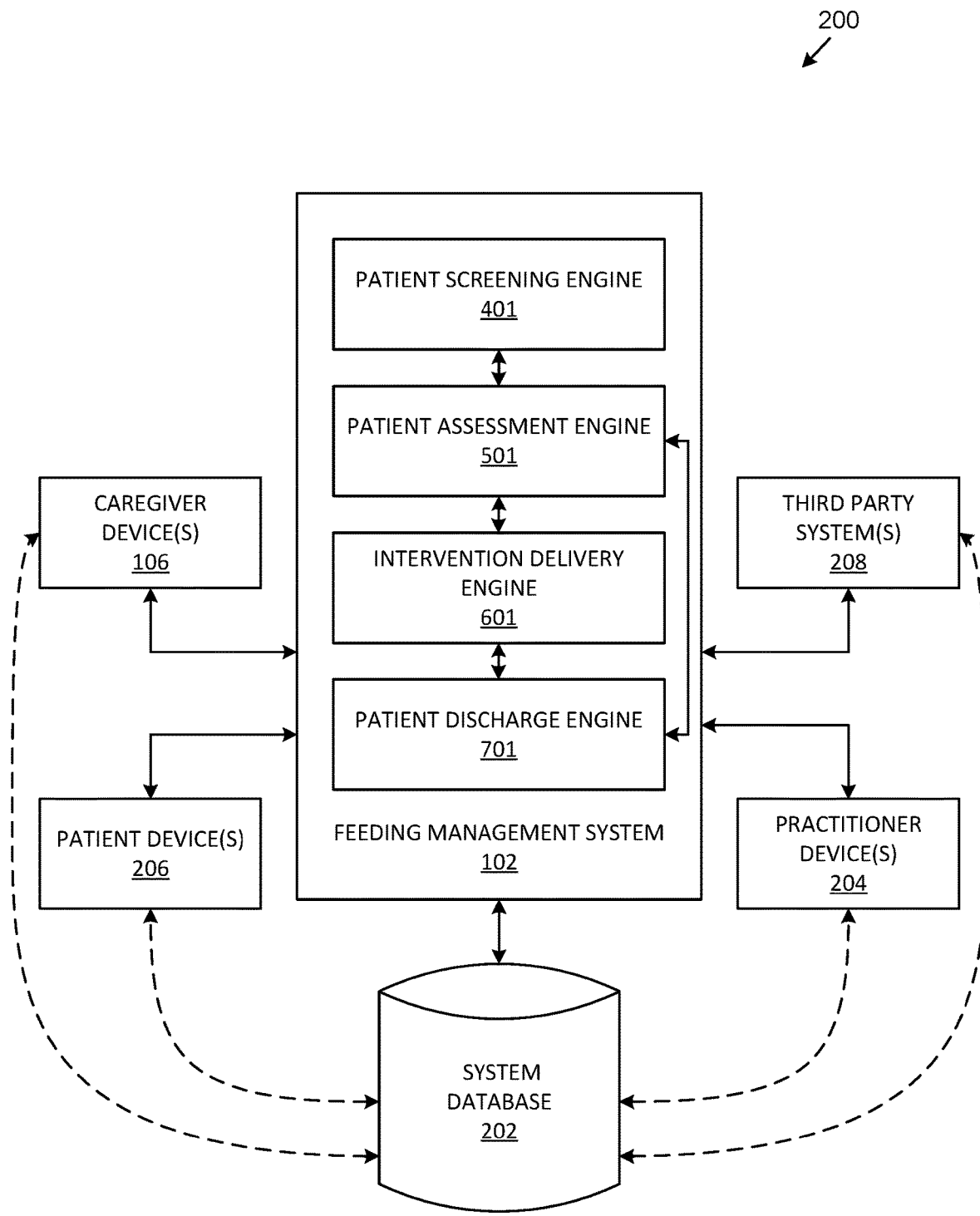
FIG 2: EXEMPLARY SYSTEM ARCHITECTURE

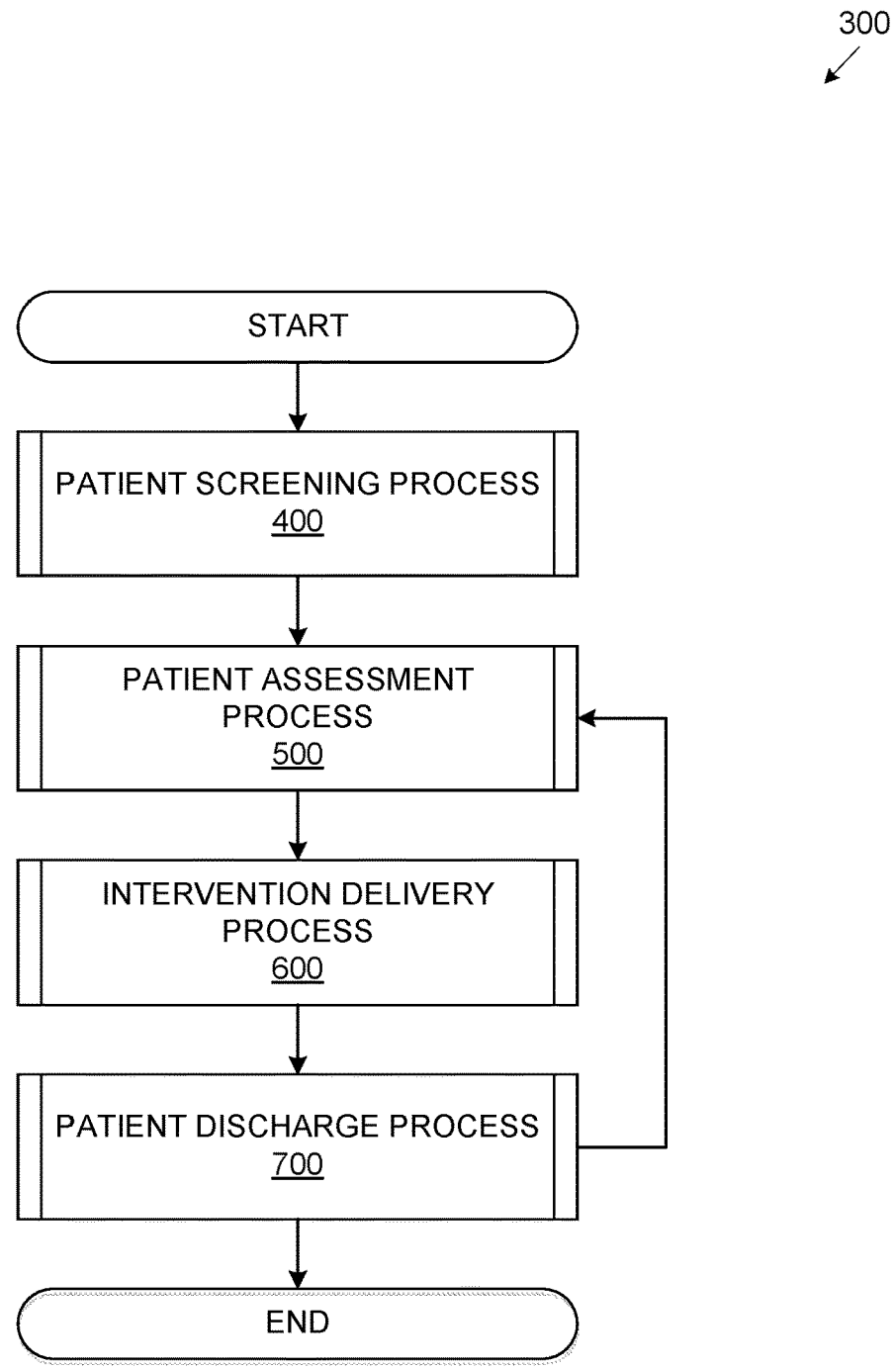
FIG 3: EXEMPLARY SYSTEM PROCESS OVERVIEW

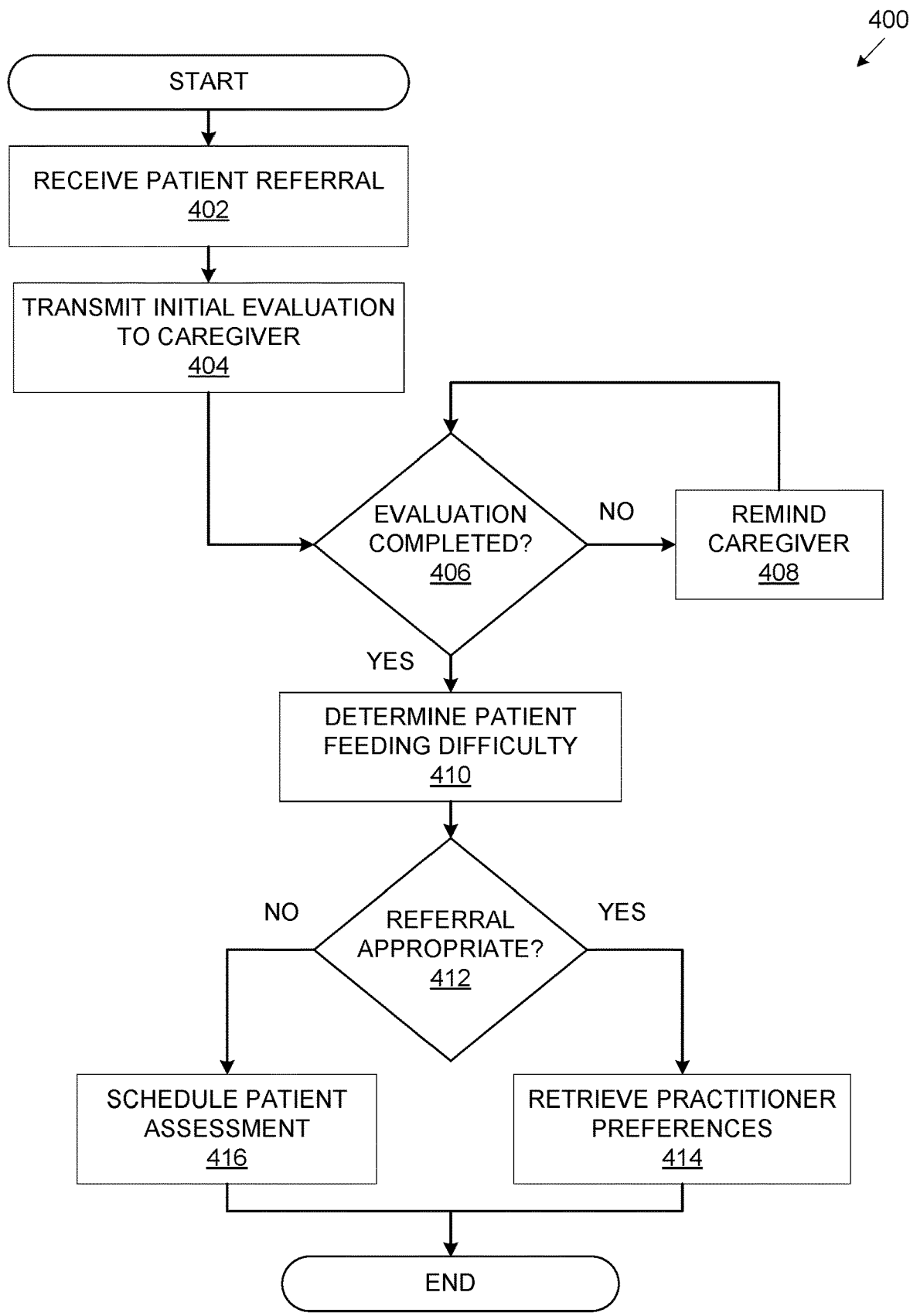
FIG 4: EXEMPLARY PATIENT SCREENING PROCESS

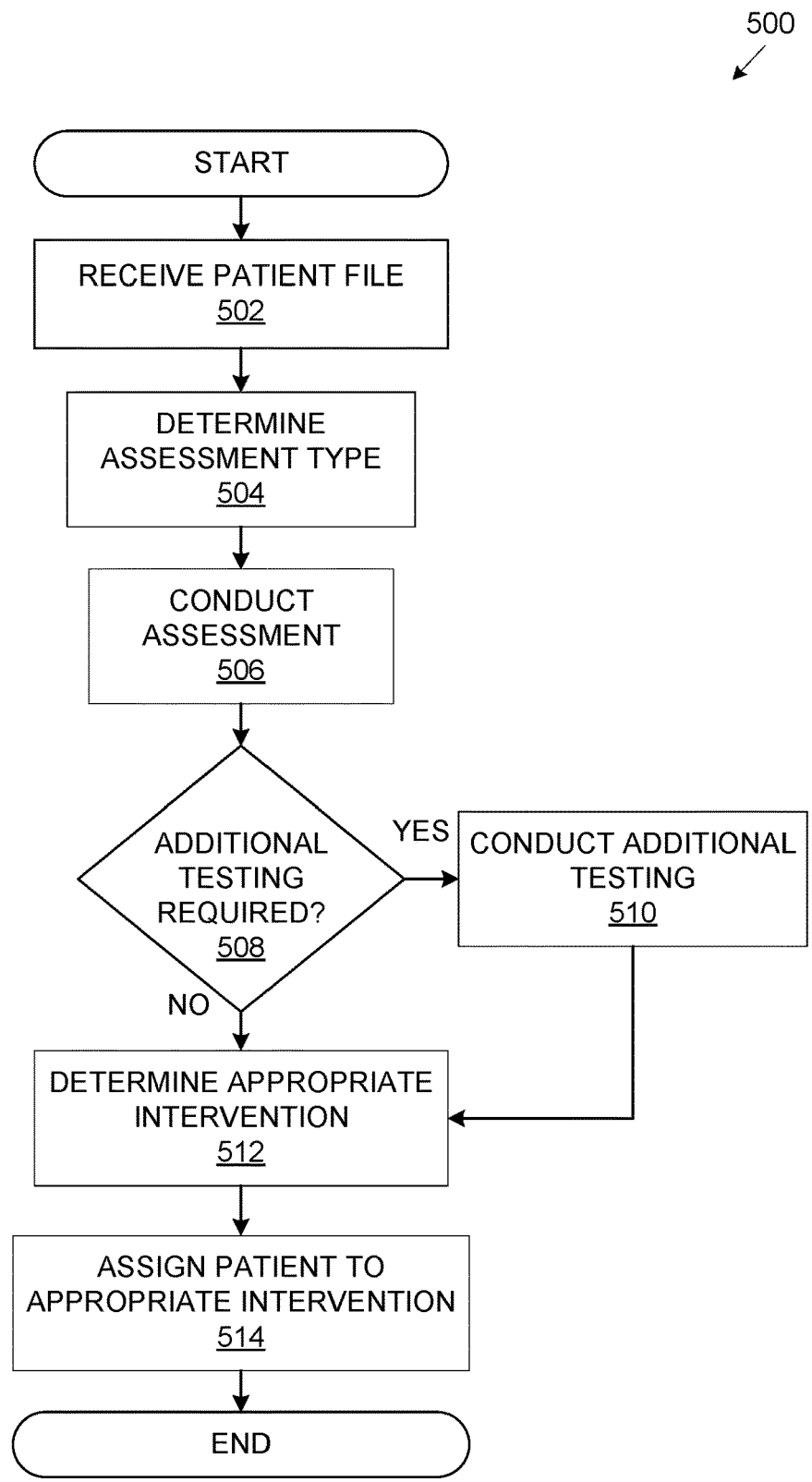
FIG 5: EXEMPLARY PATIENT ASSESSMENT PROCESS

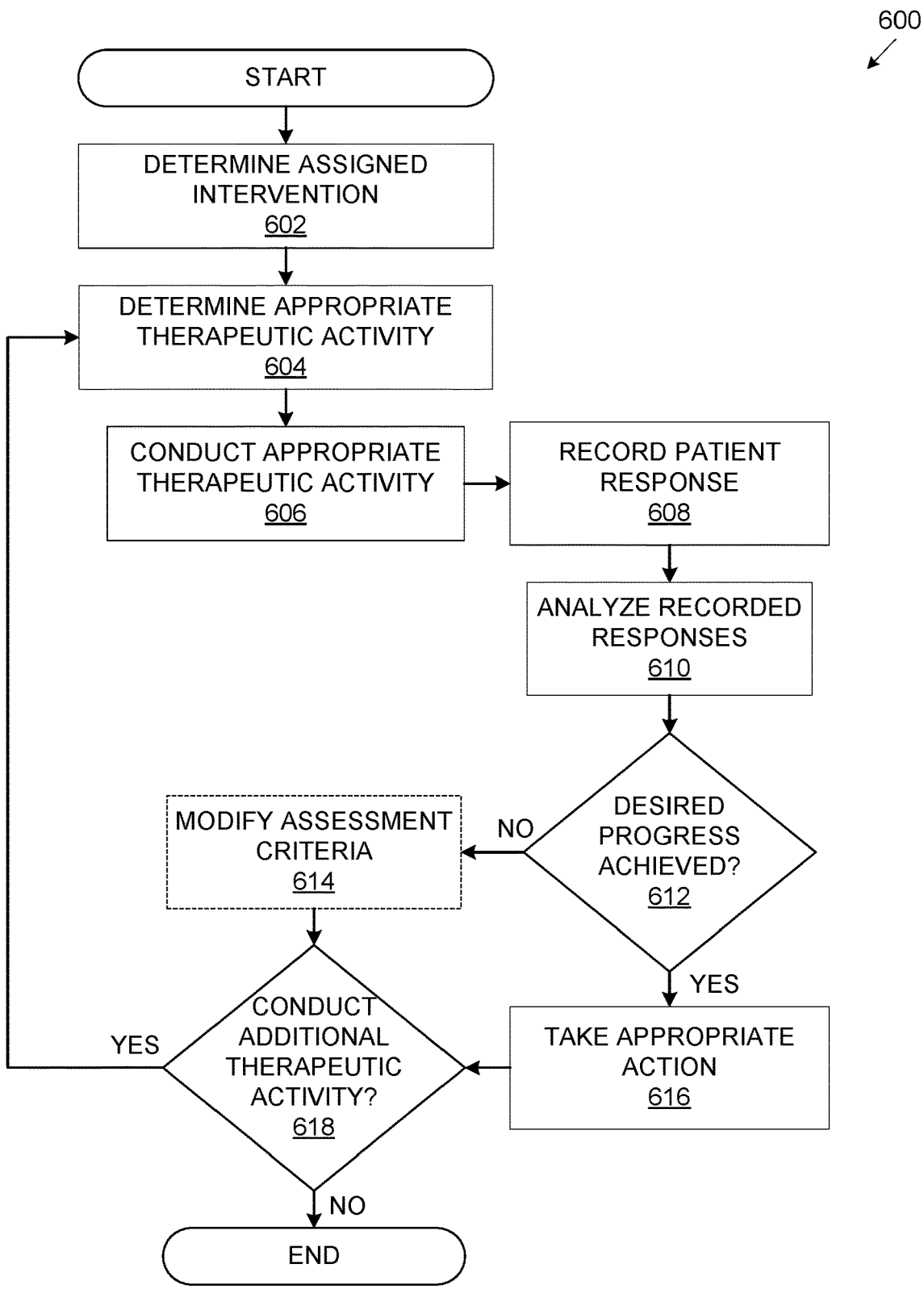
FIG 6: EXEMPLARY INTERVENTION DELIVERY PROCESS

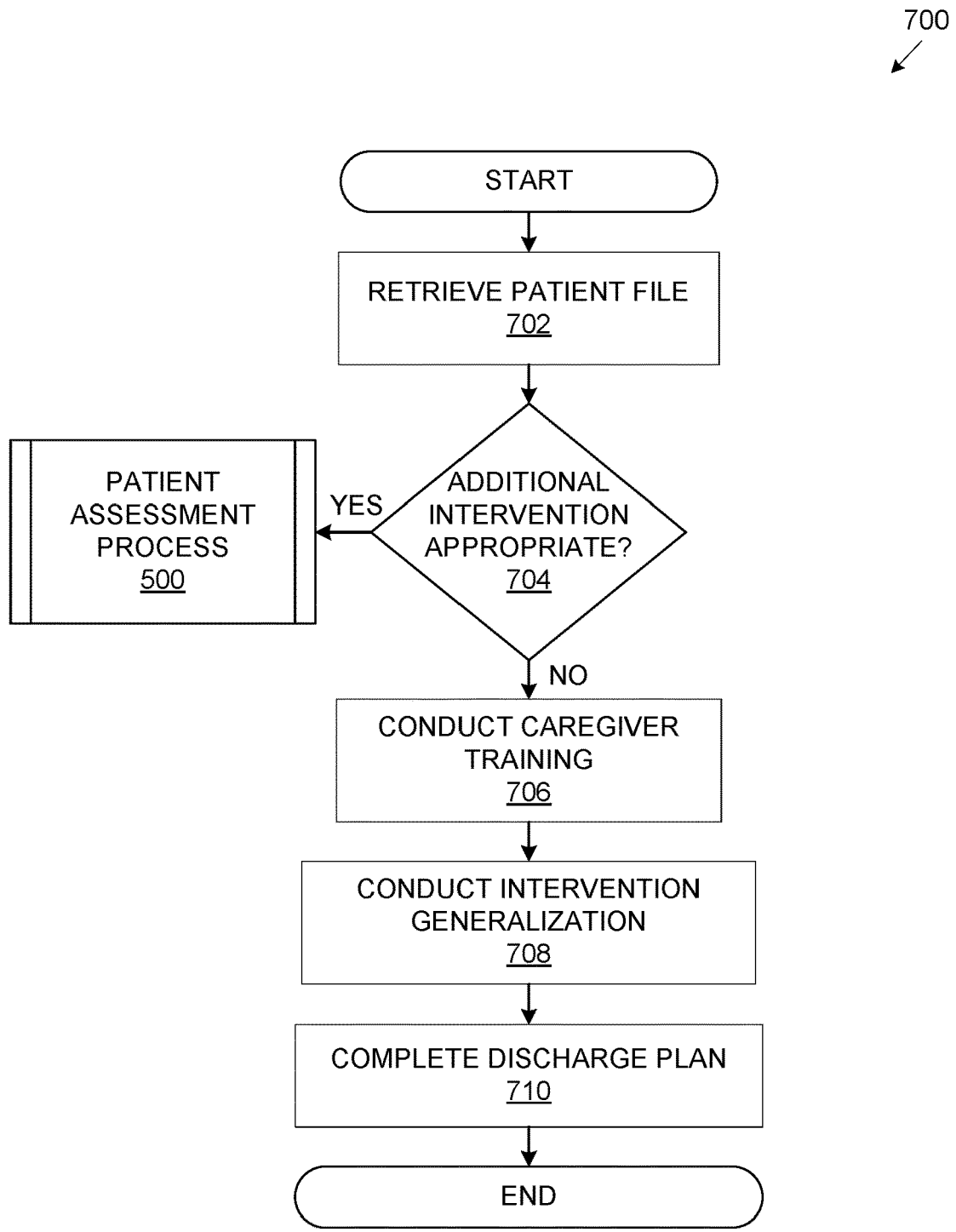
FIG 7: EXEMPLARY PATIENT DISCHARGE PROCESS

METHODS AND SYSTEMS FOR TREATMENT OF FEEDING DISORDERS

CROSS REFERENCE TO RELATED APPLICATIONS

This application claims priority to, the benefit under 35 U.S.C. § 119 of, and incorporates by reference herein in their entireties U.S. Provisional Patent Application No. 62/479,855, filed Mar. 31, 2017, and entitled "Methods and Systems for Treatment of Feeding Disorders," and U.S. Provisional Patent Application No. 62/491,538, filed Apr. 28, 2017, and entitled "Methods and Systems for Treatment of Feeding Disorders."

TECHNICAL FIELD

The present systems and methods relate generally to feeding disorders and, more particularly, to multidisciplinary treatment of feeding disorders.

BACKGROUND

Feeding disorders, which can comprise a variety of food selectivity and food avoidance behaviors, affect an individual's ability to properly function at home, school, and other social settings and may impact the individual's physical, social and psychological development. Common signs and symptoms of feeding disorders include poor weight gain, bottle, formula or feeding tube dependence, mealtime tantrums, extended meal duration (e.g., >40 minutes), distress and anxiety with new foods, inability to increase textures, inability or refusal to feed oneself, extreme pickiness (e.g., eating fewer than twelve total food items), and excessive weight gain related to patterns of severe food selectivity (e.g., a strong preference for fats, snacks, and processed foods, with a rejection of fruits and vegetables). Feeding disorders generally first emerge during infancy and early childhood but may persist into adolescence and adulthood.

Feeding disorders require treatments different from eating disorders (e.g., bulimia, anorexia, etc.) because eating disorders emerge during late childhood and early adolescence and often involve concerns about body size and shape. Treatments of these eating disorders involve a different etiology and treatment approach—most often in the form of cognitively based therapies (e.g., mindfulness training, stress reduction techniques, etc.). In contrast, due to their complexity and variety, heretofore, feeding disorders were not easily, effectively, or uniformly treated.

Therefore, there is a long-felt but unresolved need for a system or method that easily, effectively, and uniformly treats feeding disorders.

BRIEF SUMMARY OF THE DISCLOSURE

Briefly described, and according to one embodiment, aspects of the present disclosure generally relate to systems and methods for systematic treatment of feeding disorders in individuals (typically children) by a multi-disciplinary team comprising medical, behavioral, nutritional, and oral-motor skill professionals and/or specialists.

For individuals with feeding disorders, a treatment method may comprise, in various embodiments, four phases/processes: 1) screening; 2) assessment; 3) intervention; and 4) discharge. Generally, the treatment method is administered by a multi-disciplinary team comprising medical, behavioral, nutritional, and oral-motor skill professionals and/or specialists. In various embodiments, the behavioral professionals structure meal sessions using protocols and related behavioral techniques to promote intake of new foods and conduct caregiver training to support generalization of the treatment; the medical professionals assess safety to initiate feeding intervention and provide ongoing oversight of possible medical needs as oral intake of a patient advances; the nutritional professionals monitor patient growth and nutritional intake and provide oversight to ensure patients are provided with balanced nutrition, grow appropriately, and tolerate new foods; and the oral-motor skill professionals focus on oral sensitivity, building oral-motor coordination to improve the oral phase of the swallow, specifically coordination for chewing, and the introduction of new food textures.

In one embodiment, the treatment method involves up to 40 days of treatment spread over 8 weeks, depending on the severity of the feeding disorder. Treatment usually occurs over consecutive day (e.g., Monday-Friday), with multiple treatment meal sessions occurring each day (e.g., breakfast, snack, lunch, dinner). In an alternate embodiment, treatment may occur weekly or even biweekly.

During the screening process, the individual's eligibility and suitability of the treatment program are determined. In one embodiment, the screening process may involve completion of a questionnaire regarding the individual's feeding behaviors to determine whether the individual is a candidate for treatment by the program.

In the assessment process, a series of procedures may be conducted that provide the foundation for the intervention process by determining the individual's current feeding disorder to identify a potential starting point and/or key antecedent and consequence—based procedures for the intervention process. For example, a semi-structured home baseline meal observation may be conducted with a caregiver(s) serving as the feeder. Data collected during the observation may include meal structure (e.g., food presented, meal duration, bite volume, food texture, utensils, seating, etc.), caregiver behaviors (e.g., instructions, prompts, consequences, etc.), and patient response to the presentation of food (e.g., acceptance, chewing, swallowing, grams consumed, negative vocalizations, combined inappropriate behaviors, etc.). Other tasks conducted during the assessment process may include: 1) a dietitian creating a therapeutic menu of food items to target during intervention in consultation with caregivers to align with the family menu, the child's nutritional needs, and any cultural or religious dietary restrictions; 2) the feeding therapist identifying potential reinforcers that can be utilized during the intervention process; 3) the oral-motor therapist completing evaluations that provide guidance regarding appropriate seating, utensils, and other therapeutic support based on the child's medical status (e.g., oral-motor skills, appropriate food texture, etc.); 4) a physician or nurse practitioner conducting a medical history and physical to rule out and/or treatment any potential organic concerns (e.g., reflux; food allergy) that may contribute to food avoidance and/or pain associated with intake of food; 5) review of treatment approach with the caregivers conducted by a psychologist summarizing the contribution of each member of the multidisciplinary team.

The intervention process is generally divided into two major parts: 1) treatment development and refinement; and 2) treatment implementation and progression toward goals. During treatment development and refinement, core treatment elements are identified, the overall treatment is established, and the treatment is refined and adjusted based on the child's response to meal session and new information yielded during the course of treatment, with support provided from each discipline. Detailed mealtime protocols and data collection procedures may be developed to help guide how treatment elements are combined and integrated into meal sessions. Discipline specific (e.g., psychology, medicine, nutrition, oral, oral-motor, etc.) assessment and treatment contributions are generally guided by algorithms (e.g., machine-learning, etc.) and decision pathways. During treatment implementation and progression toward goals, each patient's progress is recorded and tracked as the treatment shifts toward advancing core goals for the patient (e.g., increasing oral intake, expanding dietary variety, addressing underlying nutritional deficiencies, and/or promoting independence during meals). Generally, during the intervention process, patients may follow a standard schedule of treatment "doses" per day (e.g., four 40-minute treatment meal sessions, six 15-minute treatment meal sessions, etc.). Meal sessions may generally be spaced to provide adequate time for digestion to occur, with potentially long breaks between lunch and dinner for small children to nap.

During the discharge process, caregivers undergo systematic training on the feeding protocol and the multidisciplinary team provides support to assure generalization and maintenance of treatment gains following discharge, which may include conducing home visits, formal discharge planning, and planning for step down services, for example, from day treatment to an outpatient clinic.

In one embodiment, treatment meal sessions may occur in a private treatment room with an adjacent observation room. During a session, the subject sits in age-appropriate seating (e.g., highchair, booster seat, etc.). A session may target a total of 16 foods items (e.g., four fruits, four vegetables, four starches, and four meats) plus a nutritionally complete drink. The feeding therapist may randomly select one food from each group and randomly present these four foods at a designated texture (e.g., puree, etc.) and bite volume (e.g., half-level bolus size, etc.). Generally, the order of food item presentation remains the same within a given session. In one embodiment, the next food item presented to the patient is determined based on the patient's response to the current food item. For example, if the patient accepts the food, then the food may be presented to the patient again. If, however, the patient rejects the food, then a different food may be selected and presented to the patient. Generally, a treatment meal session may not end until all of the different food items have been presented to the patient.

In various embodiments, the present disclosure represents an improvement in treatment of feeding disorders because it is systematic, easy to implement, and effective, regardless of the feeding disorder/feeding behaviors presented by the patient, as exemplified by detailed data collection procedures, standardized treatment protocols, formalized decision rules, and patient-specific intervention. For example, the use of operational definitions permits recording of mealtime performance (e.g., bite acceptance, swallowing, crying, disruptions, etc.). Data may be aggregated into five bite sessions, which allows for analysis of trends and progress using percentages. Similarly, feeding protocols may outline the sequence of steps and structure of mealtime interactions. Standardization may comprise scripted instructions, uniform bite volume, pre-specified persistence when presenting mealtime demands, and consequences for appropriate and inappropriate mealtime behaviors. Further, the introduction of treatment elements may be guided by decision rules which consider: 1) the patient's response to the current mealtime protocol reflected in the data collection process, and 2) current target of feeding intervention based on the patient's refusal topography (e.g., accepting bites, retention of food, swallowing, etc.). Finally, the sequencing of techniques introduced during intervention unfolds in a manner that allows intervention to share core features across patients (e.g., bite spacing, use of praise, meal duration, etc.), while also allowing for flexibility in combining treatment elements to meet an individual patient's needs.

In one embodiment, a method for treating one or more feeding disorders in a human to improve one or more feeding behaviors of the human, comprising the steps of: assessing the human to determine the one or more feeding disorders to be treated and the one or more feeding behaviors of the human; comparing the one or more feeding behaviors of the human and the one or more feeding disorders with one or more predefined rules to determine an intervention that will treat the one or more feeding disorders and will improve the one or more feeding behaviors of the human; conducting the determined intervention, wherein the determined intervention comprises at least a meal session during which a feeder presents a bite of food using a feeding utensil to the human and records the response of the human to the bite of food; determining, based on the recorded response, whether to conduct an additional intervention, wherein an additional intervention is appropriate if the recorded response does not demonstrate an improvement in the one or more feeding behaviors that meets a predetermined threshold; and upon determining not to conduct the additional intervention, discharging the human.

In one embodiment, a system for treating one or more feeding disorders in a human to improve one or more feeding behaviors of the human, comprising: a caregiver electronic computing device that generates an evaluation regarding the feeding disorders of the human and transmits the evaluation to a feeding management system; the feeding management system that receives the evaluation from the caregiver electronic computing device and determines the one or more feeding orders to be treated and, based on the one or more feeding orders, transmits a request to a practitioner electronic computing device for an assessment of the one or more feeding behaviors of the human; the practitioner electronic computing device that receives the request for the assessment from the feeding management system, generates the assessment, and transmits the assessment to the feeding management system; the feeding management system that receives the assessment from the practitioner electronic computing device and determines, based on a comparison of the evaluation and the assessment with one or more predefined rules, an intervention that will treat the one or more feeding disorders and will improve the one or more feeding behaviors of the human, wherein the determined intervention comprises a meal session during which a feeder presents a bite of food using a feeding utensil to the human and records the response of the human to the bite of food using the practitioner electronic computing device; the practitioner electronic computing device that receives the response and transmits the response to the feeding management system; and the feeding management system that: receives the response from the practitioner electronic computing device; determines, based on the response, whether to conduct an additional intervention, wherein an additional intervention is appropriate if the response does not demonstrate an improvement in the one or more feeding behaviors that meets a predetermined threshold; and upon determining not to conduct the additional intervention, discharges the human.

According to one aspect of the present disclosure, the method, wherein the one or more feeding disorders are selected from a list comprising food refusal and food selectivity. Furthermore, the method, wherein the one or more feeding behaviors of the human are selected from a list comprising choking, gagging, vomiting, difficulty swallowing, oral-motor deficiencies, and tantrums. Moreover, the method, wherein the determined intervention further comprises an occupational and speech therapist session during which the human improves oral-motor coordination. Further, the method, further comprising the steps of: prior to determining not to conduct the additional intervention, determining to conduct the additional intervention; upon determining to conduct the additional intervention, conducting an additional meal session; recording a result of the additional meal session; and determining, based on the recorded result and the recorded response, whether to conduct the determined intervention again. Additionally, the method, wherein the recorded response and the recorded result are selected from a list comprising acceptance, disruption, and grams of food consumed. Also, the method, wherein acceptance is recorded when at least half of the feeding utensil enters the human's mouth.

According to one aspect of the present disclosure, the method, wherein disruption is recorded when the human rejects the feeding utensil by turning its head away from the feeding utensil, pushing away the feeding utensil, or pushing away a hand of the feeder holding the feeding utensil. Furthermore, the method, wherein the additional meal session further comprises the steps of: a) presenting to the human a first bite of a first food selected from a menu of food based on the one or more feeding disorders and the one or more feeding behaviors; b) based on the human's acceptance or disruption, either presenting the first bite another time or presenting a first bite of a different food selected from the menu of food; and c) repeating step b until at least one bite of each of the foods from the menu of food has been presented to the human. Moreover, the method, wherein the first bite of the first food is a volume of food from about 0.2 cm$^3$ to about 3.0 cm$^3$. Further, the method, wherein the volume of food is increased when the rate of the human accepting the first bite is higher than a previous rate or is stable. Additionally, the method, wherein the first food is pureed. Also, the method, wherein the predetermined threshold comprises consuming a predetermined number of grams, based on the age of the human, of each of the foods from the menu of food and wherein discharging the human further comprises the steps of: conducting the meal session in a familiar setting of the human under the observation of the caregiver; teaching the caregiver to perform the meal session in the familiar setting; and teaching the caregiver to prepare each of the foods from the menu of food.

According to one aspect of the present disclosure, the system, wherein the one or more feeding disorders are selected from a list comprising food refusal and food selectivity. Furthermore, the system, wherein the one or more feeding behaviors of the human are selected from a list comprising choking, gagging, vomiting, difficulty swallowing, oral-motor deficiencies, and tantrums. Moreover, the system, wherein the determined intervention further comprises an occupational and speech therapist session during which the human improves oral-motor coordination. Further, the system, wherein the feeding management system: prior to determining not to conduct the additional intervention, determines to conduct the additional intervention; upon determining to conduct the additional intervention, conducts an additional meal session; receives a recorded result of the additional meal session from the practitioner electronic computing device; and determines, based on the recorded result and the recorded response, whether to conduct the determined intervention again. Additionally, the system, wherein the recorded response and the recorded result are selected from a list comprising acceptance, disruption, and grams of food consumed. Also, the system, wherein acceptance is recorded when at least half of the feeding utensil enters the human's mouth.

According to one aspect of the present disclosure, the system, wherein disruption is recorded when the human rejects the feeding utensil by turning its head away from the feeding utensil, pushing away the feeding utensil, or pushing away a hand of the feeder holding the feeding utensil. Furthermore, the system, wherein the additional meal session further comprises: a) presenting to the human a first bite of a first food selected from a menu of food based on the one or more feeding disorders and the one or more feeding behaviors; b) based on the human's acceptance or disruption, either presenting the first bite another time or presenting a first bite of a different food selected from the menu of food; and c) repeating step b until at least one bite of each of the foods from the menu of food has been presented to the human. Moreover, the system, wherein the first bite of the first food is a volume of food from about 0.2 cm$^3$ to about 3.0 cm$^3$. Further, the system, wherein the volume of food is increased when the rate of the human accepting the first bite is higher than a previous rate or is stable. Additionally, the system, wherein the first food is pureed. Also, the system, wherein the predetermined threshold comprises consuming a predetermined number of grams, based on the age of the human, of each of the foods from the menu of food.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 1 illustrates an exemplary, high-level overview of one embodiment of the disclosed system.

FIG. 2 illustrates an exemplary system architecture, according to one embodiment of the present disclosure.

FIG. 3 is a flowchart showing an exemplary system process, according to one embodiment of the present disclosure.

FIG. 4 is a flowchart showing an exemplary patient screening process, according to one embodiment of the present disclosure.

FIG. 5 is a flowchart showing an exemplary patient assessment process, according to one embodiment of the present disclosure.

FIG. 6 is a flowchart showing an exemplary intervention delivery process, according to one embodiment of the present disclosure.

FIG. 7 is a flowchart showing an exemplary patient discharge process, according to one embodiment of the present disclosure.

DETAILED DESCRIPTION

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to systems and methods for systematic treatment of feeding disorders in individuals (typically children) by a multi-disciplinary team comprising medical, behavioral, nutritional, and oral-motor skill professionals and/or specialists.

For individuals with feeding disorders, a treatment method may comprise, in various embodiments, four phases/processes: 1) screening; 2) assessment; 3) intervention; and 4) discharge. Generally, the treatment method is administered by a multi-disciplinary team comprising medical, behavioral, nutritional, and oral-motor skill professionals and/or specialists. In various embodiments, the behavioral professionals structure meal sessions using protocols and related behavioral techniques to promote intake of new foods and conduct caregiver training to support generalization of the treatment; the medical professionals assess safety to initiate feeding intervention and provide ongoing oversight of possible medical needs as oral intake of a patient advances; the nutritional professionals monitor patient growth and nutritional intake and provide oversight to ensure patients are provided with balanced nutrition, grow appropriately, and tolerate new foods; and the oral-motor skill professionals focus on oral sensitivity, building oral-motor coordination to improve the oral phase of the swallow, specifically coordination for chewing, and the introduction of new food textures.

In one embodiment, the treatment method involves up to 40 days of treatment spread over 8 weeks, depending on the severity of the feeding disorder. Treatment usually occurs over consecutive day (e.g., Monday-Friday), with multiple treatment meal sessions occurring each day (e.g., breakfast, snack, lunch, dinner). In an alternate embodiment, treatment may occur weekly or even biweekly.

During the screening process, the individual's eligibility and suitability of the treatment program are determined. In one embodiment, the screening process may involve completion of a questionnaire regarding the individual's feeding behaviors to determine whether the individual is a candidate for treatment by the program.

In the assessment process, a series of procedures may be conducted that provide the foundation for the intervention process by determining the individual's current feeding disorder to identify a potential starting point and/or key antecedent and consequence-based procedures for the intervention process. For example, a semi-structured home baseline meal observation may be conducted with a caregiver(s) serving as the feeder. Data collected during the observation may include meal structure (e.g., food presented, meal duration, bite volume, food texture, utensils, seating, etc.), caregiver behaviors (e.g., instructions, prompts, consequences, etc.), and patient response to the presentation of food (e.g., acceptance, chewing, swallowing, grams consumed, negative vocalizations, combined inappropriate behaviors, etc.). Other tasks conducted during the assessment process may include: 1) a dietitian creating a therapeutic menu of food items to target during intervention in consultation with caregivers to align with the family menu, the child's nutritional needs, and any cultural or religious dietary restrictions; 2) the feeding therapist identifying potential reinforcers that can be utilized during the intervention process; 3) the oral-motor therapist completing evaluations that provide guidance regarding appropriate seating, utensils, and other therapeutic support based on the child's medical status (e.g., oral-motor skills, appropriate food texture, etc.); 4) a physician or nurse practitioner conducting a medical history and physical to rule out and/or treatment any potential organic concerns (e.g., reflux; food allergy) that may contribute to food avoidance and/or pain associated with intake of food; 5) review of treatment approach with the caregivers conducted by a psychologist summarizing the contribution of each member of the multidisciplinary team.

The intervention process is generally divided into two major parts: 1) treatment development and refinement; and 2) treatment implementation and progression toward goals. During treatment development and refinement, core treatment elements are identified, the overall treatment is established, and the treatment is refined and adjusted based on the child's response to meal session and new information yielded during the course of treatment, with support provided from each discipline. Detailed mealtime protocols and data collection procedures may be developed to help guide how treatment elements are combined and integrated into meal sessions. Discipline specific (e.g., psychology, medicine, nutrition, oral, oral-motor, etc.) assessment and treatment contributions are generally guided by algorithms (e.g., machine-learning, etc.) and decision pathways. During treatment implementation and progression toward goals, each patient's progress is recorded and tracked as the treatment shifts toward advancing core goals for the patient (e.g., increasing oral intake, expanding dietary variety, addressing underlying nutritional deficiencies, and/or promoting independence during meals). Generally, during the intervention process, patients may follow a standard schedule of treatment "doses" per day (e.g., four 40-minute treatment meal sessions, six 15-minute treatment meal sessions, etc.). Meal sessions may generally be spaced to provide adequate time for digestion to occur, with potentially long breaks between lunch and dinner for small children to nap.

During the discharge process, caregivers undergo systematic training on the feeding protocol and the multidisciplinary team provides support to assure generalization and maintenance of treatment gains following discharge, which may include conducing home visits, formal discharge planning, and planning for step down services, for example, from day treatment to an outpatient clinic.

In one embodiment, treatment meal sessions may occur in a private treatment room with an adjacent observation room. During a session, the subject sits in age-appropriate seating (e.g., highchair, booster seat, etc.). A session may target a total of 16 foods items (e.g., four fruits, four vegetables, four starches, and four meats) plus a nutritionally complete drink. The feeding therapist may randomly select one food from each group and randomly present these four foods at a designated texture (e.g., puree, etc.) and bite volume (e.g., half-level bolus size, etc.). Generally, the order of food item presentation remains the same within a given session. In one embodiment, the next food item presented to the patient is determined based on the patient's response to the current food item. For example, if the patient accepts the food, then the food may be presented to the patient again. If, however, the patient rejects the food, then a different food may be selected and presented to the patient. Generally, a treatment meal session may not end until all of the different food items have been presented to the patient.

In various embodiments, the present disclosure represents an improvement in treatment of feeding disorders because it is systematic, easy to implement, and effective, regardless of the feeding disorder/feeding behaviors presented by the patient, as exemplified by detailed data collection procedures, standardized treatment protocols, formalized decision rules, and patient-specific intervention. For example, the use of operational definitions permits recording of mealtime performance (e.g., bite acceptance, swallowing, crying, disruptions, etc.). Data may be aggregated into five bite sessions, which allows for analysis of trends and progress using percentages. Similarly, feeding protocols may outline the sequence of steps and structure of mealtime interactions. Standardization may comprise scripted instructions, uniform bite volume, pre-specified persistence when presenting mealtime demands, and consequences for appropriate and inappropriate mealtime behaviors. Further, the introduction of treatment elements may be guided by decision rules which consider: 1) the patient's response to the current mealtime protocol reflected in the data collection process, and 2) current target of feeding intervention based on the patient's refusal topography (e.g., accepting bites, retention of food, swallowing, etc.). Finally, the sequencing of techniques introduced during intervention unfolds in a manner that allows intervention to share core features across patients (e.g., bite spacing, use of praise, meal duration, etc.), while also allowing for flexibility in combining treatment elements to meet an individual patient's needs.

Exemplary Embodiments

Referring now to the figures, for the purposes of example and explanation of the fundamental processes and components of the disclosed systems and methods, reference is made to FIG. 1, which illustrates an exemplary, high-level overview 100 of one embodiment of the feeding management process and system 102. As will be understood and appreciated, the exemplary, high-level overview 100 shown in FIG. 1 represents merely one approach or embodiment of the present system, and other aspects are used according to various embodiments of the present system. Generally, by way of example, and not by way of limitation, a high-level overview of actions involved in an exemplary system process is shown in FIG. 1 with the help of a sequence of numbered steps indicated as steps "A" through "D," which are annotated in circles.

In various embodiments, the feeding management system 102 treats individuals with feeding disorders (e.g., food refusal, food selectivity, etc.) to improve the individual's diet (e.g., increasing the quantity, type, and/or texture of foods eaten), and feeding behaviors (e.g., reducing choking, gagging, vomiting, difficulty swallowing, oral-motor deficiencies, tantrums, etc.). In one non-limiting example, at step A, a caregiver 104 completes, using an electronic computing device 106, a screening questionnaire regarding the feeding habits and/or behaviors of a child 108 in his/her care (e.g., the child 108 also referred to herein as a patient, human, etc., as this disclosure places no limitation on the age of the individuals with feeding disorders that may be treated). Generally, this questionnaire may inquire as to the types of food eaten by the child 108, type of foods avoided, meal duration, meal frequency, allergies, previous treatments received, other medical diagnoses, etc. so that the child 108 may be screened for eligibility for treatment using/facilitated by the feeding management system 102.

Thus, between steps A and B, the completed screening questionnaire is reviewed by the feeding management system 102 and/or a medical practitioner 110 (e.g., doctor, nurse, behavioral psychologist, nutritionist, occupational therapist, speech therapist, gastroenterologist, social worker, etc.) to determine if the child 108 is eligible for treatment with the feeding management system 102. If the child 108 is eligible for treatment, then, in one embodiment at step B, one or more medical practitioners 110 assess/evaluate a feeding of the child 108 by his/her caregiver 104 in a familiar environment (e.g., home, etc.) to gather data that will be used to develop an intervention/treatment plan for the child 108 to advance one or more core goals (e.g., increasing oral intake, expanding dietary variety, addressing underlying nutritional deficiencies, promoting independence during meals, etc.). Generally, the number of medical practitioners 110 assessing the feeding depends on the data collected in the screening questionnaire—with more complex cases receiving larger teams of medical practitioners 110 to complete the initial assessment. In one embodiment, each medical practitioner 110 evaluates the feeding of the child 108 based on his/her respective area of expertise—for example, reviewing past and current feeding behaviors and practices, medial history, anthropometric trends, biochemical data, gastrointestinal concerns, dietary variety, dietary intake patterns, oral-motor developmental skill level, etc.

Based on the initial assessment, the intervention/treatment plan is developed for the child 108 by the feeding management system 102 and/or the medical practitioner(s) 110. In various embodiments, the plan may involve an intensive day treatment program spread over at least 40 consecutive business days, an outpatient treatment program that provides weekly treatment to the child 108, or a referral to an outside provider. Thus, at step C in various embodiments, the child 108 receives the intervention from the medical practitioner(s) 110. The intervention is generally divided into two major parts: 1) treatment development and refinement; and 2) treatment implementation and progression toward goals. During treatment development and refinement, core treatment elements are identified, the overall treatment is established, and the treatment is refined and adjusted based on the response of the child 108 to meal sessions. During treatment implementation and progression toward goals, the progress of the child 108 is recorded and tracked as the treatment shifts toward advancing the core goals for the child 108. Generally, a standard schedule of treatment "doses" per day (e.g., four 40-minute treatment meal sessions per day/visit, etc.) may be given to the child 108 by a medical practitioner 110.

Once the child 108 has achieved one or more of the core goals or progression towards the cord goals has stabilized, then the child 108, at step D in one embodiment, may be discharged from the intervention/treatment plan. Generally, discharge may involve moving the child 108 to a different treatment plan (e.g., from intensive day treatment to outpatient treatment, from outpatient treatment to a referral to an outside provider, etc.) or generalization of the intervention/ treatment plan so that the caregiver 104 may continue the progress achieved by the treatment plan. In one embodiment, generalization involves a medical practitioner 110 instructing the caregiver 104 on how to feed the child 108 (e.g., how to prepare the food, how to present the food, how to correct undesired feeding behaviors, etc.). Similarly, in one embodiment, generalization may involve slowly getting the child 108 accustomed to eating in a new environment.

Generally, after discharge, the treatment of the child 108 is complete. In one embodiment, however, the medical practitioner(s) 110 may continue to monitor the progress of the child through reports from the caregiver 108—providing suggestions on how to combat new feeding behaviors, etc.

Now referring to FIG. 2, an exemplary system architecture 200 is shown according to one embodiment of the present disclosure. The exemplary architecture 200 in FIG. 2 is shown for illustrative purposes only and could comprise only one engine, module, device, or collection of code, etc. In one embodiment, the feeding management system 102 is operatively connected to one or more practitioner devices 204, one or more caregiver devices 106, one or more patient devices 206, one or more system databases 202, and one or more third party systems 208 via a network(s) to help conduct the processes disclosed herein. Generally, the network(s), not shown in FIG. 2, may comprise any connection capable of transferring data between two or more computer systems (e.g., a secure or unsecured connection, Bluetooth, wireless or wired local-area networks (LANs), cell network, the Internet, etc.).

In various embodiments, the practitioner device 204 is any device that is capable of performing the functionality disclosed herein (e.g., desktop computer, laptop computer, tablet computer, smartphone, medical device, scale, food preparation device, feeding device, highchair, booster seat, table, feeding utensils, small spoon, massaging brush, rubber-coated baby spoon, bib, serving tray, intake log, etc.). In one embodiment, the practitioner device 204 facilitates treatment of a patient and optionally communicates via a network(s) with the system 102 and/or the system database 202 to provide data regarding the assessment, treatment, and discharge of patients (e.g., as part of processes 500, 600, and 700, further details of which will be discussed in association with the description of FIGS. 3, 5, 6, and 7). The practitioner device 204 may automatically collect data regarding the patient or may receive manual input of data regarding the patient or a combination thereof.

In various embodiments, the caregiver device 106 is any device that is capable of performing the functionality disclosed herein (e.g., desktop computer, laptop computer, tablet computer, smartphone, scale, food preparation device, feeding device, highchair, booster seat, table, feeding utensils, small spoon, massaging brush, rubber-coated baby spoon, bib, serving tray, etc.). The caregiver device 106, in various embodiments, facilitates feeding of a patient and optionally communicates via a network(s) with the system 102 and/or the system database 202 to provide data regarding the screening and discharge of the patient (e.g., as part of processes 400 and 700, further details of which will be discussed in association with the description of FIGS. 4 and 7).

In various embodiments, the patient device 206 is any device that is capable of performing the functionality disclosed herein (e.g., desktop computer, laptop computer, tablet computer, smartphone, feeding device, highchair, booster seat, table, feeding utensils, small spoon, massaging brush, rubber-coated baby spoon, bib, serving tray, etc.). The patient device 206, in various embodiments, facilitates feeding of the patient and optionally communicates via a network(s) with the system 102 and/or the system database 202 to provide data regarding the assessment, treatment, and discharge of patients (e.g., as part of processes 500, 600, and 700, further details of which will be discussed in association with the description of FIGS. 3, 5, 6, and 7).

Still referring to FIG. 2, the system database 202, in various embodiments, may be any computing device (e.g., desktop computer, laptop, servers, tablets, etc.), combination of computing devices, software, hardware, combination of software and hardware, database (e.g., stored in the cloud or on premise, structured as relational, etc.), or combination of databases that is capable of performing the functionality disclosed herein. In one embodiment, the system database 202 is local to the practitioner device 204 or system 102 (e.g., the system 102 comprises the system database 202, etc.). In other embodiments, the system database 202 is virtual or stored in the "cloud." In various embodiments, the system database 202 communicates via a network(s) with the system 102, practitioner device 204, caregiver device 106, patient device 206, and third party systems 208 to store determined interventions, patient profiles, practitioner preferences, treatment rules, assessment rules, etc. In one embodiment, the system database 202 is updated dynamically and/or in real time to provide data to a practitioner regarding a patient.

In various embodiments, the third party system 208 may be any computing device (e.g., desktop computer, laptop, servers, tablets, etc.), combination of computing devices, software, hardware, combination of software and hardware, database (e.g., stored in the cloud or on premise, structured as relational, etc.), or combination of databases that is capable of performing the functionality disclosed herein (e.g., patient portals, electronic medical records systems, etc.). In one embodiment, the third party systems 208 provide additional information for the screening, assessment, treatment, and discharge of patients (e.g., as part of processes 400, 500, 600, and 700, further details of which will be discussed in association with the description of FIGS. 3-7).

Generally, the system 102 (and its engines) may be any computing device (e.g., desktop computer, laptop, servers, tablets, etc.), combination of computing devices, software, hardware, or combination of software and hardware that is capable of performing the functionality disclosed herein. In various embodiments, the system 102 may comprise a patient screening engine 401, patient assessment engine 501, intervention delivery engine 601, and patient discharge engine 701. In one embodiment, the patient screening engine 401 conducts the patient screening process (further details of which will be discussed in association with the description of FIG. 4) and communicates with the patient assessment engine 501. The patient assessment engine 501, in one embodiment, conducts the patient assessment process (further details of which will be discussed in association with the description of FIG. 5) and communicates with the patient screening engine 401, intervention delivery engine 601, and patient discharge process 701. In one embodiment, the intervention delivery engine 601 conducts the intervention delivery process (further details of which will be discussed in association with the description of FIG. 6) and communicates with the patient assessment engine 501 and patient discharge engine 701. The patient discharge engine 701, in one embodiment, conducts the patient discharge process (further details of which will be discussed in association with the description of FIG. 7) and communicates with the intervention delivery engine 601 and patient assessment engine 501.

In various embodiments, the engines (401, 501, 601, and 701) may be used to guide practitioners, suggest approaches, collected and organize data, manage protocols, etc. Generally, the engines are used by a user on a device (e.g., iPad, etc.) such as caregiver device 106, practitioner device 204, etc.

Referring now to FIG. 3, an exemplary system process 300 is shown according to one embodiment of the present disclosure. Generally, the system process 300 is the process by which the system 102 (from FIG. 1) is used to treat patients 108 (from FIG. 1) with feeding disorders. As will be understood by one having ordinary skill in the art, the steps and processes shown in FIG. 3 (and those of all other flowcharts and sequence diagrams shown and described herein) may operate concurrently and continuously, are generally asynchronous and independent, and are not necessarily performed in the order shown. Further, although reference herein is generally made to actions performed by the system, all actions are understood to also be intended to be performed by a medical practitioner 110 (from FIG. 1) or other system user with or without the assistance of the system. In particular, some processes are conducted by users, some by system components, etc., depending on the particular embodiment.

In various embodiments, the system process 300 begins with the patient screening process 400, wherein the system receives information from the caregiver 104 (from FIG. 1) regarding the patient's feeding behaviors (further details of which will be explained in association with the description of FIG. 4). Generally, the patient screening process 400 permits the system and/or the medical practitioner(s) to determine whether the patient is eligible for the treatment disclosed herein.

If the patient is eligible for the treatment disclosed herein, the system proceeds to the patient assessment process 500. Generally, the patient assessment process 500 is the process by which the patient's feeding behaviors are assessed by one or more medical practitioners to develop an intervention for the patient (further details will be explained in association with the description of FIG. 5). In one embodiment, wherein the patient's feeding disorder is less severe, the patient assessment process 500 is only conducted by a single medical practitioner. In one embodiment, wherein the patient's feeding disorder is more severe, the patient assessment process 500 is conducted by multiple medical practitioners of varying expertise (e.g., behavioral psychologist, nutritionist, occupational therapist, speech therapist, gastroenterologist, social worker, etc.). The patient assessment process 500 may be conducted by observing a feeding of the patient by the caregiver in a location familiar to the patient (e.g., home, school, etc.).

Based on the results of the patient assessment process 500, the determined intervention is provided to the patient as part of the intervention delivery process 600 (further details of which will be explained in association with the description of FIG. 6). Generally, the intervention may involve an intensive day treatment program that provides daily treatment to the patient in a specialized facility, an outpatient treatment program that provides weekly treatment to the patient in a specialized facility, or a referral to an outside provider that provides treatment to the patient as needed either in the outside provider's facility or the patient's home. In various embodiments, an appropriate activity is determined for the patient, presented to the patient by one or more medical practitioners, and the results of activity are recorded so the next appropriate action may be determined. For example, in one embodiment, the activity may comprise a standard schedule of treatment "doses" per day (e.g., four 40-minute treatment meal sessions per day/visit, wherein the patient is presented with food of different types, temperatures, textures, etc.). In some embodiments, the activity is repeated until the patient's feeding disorder has been treated or reduced. In various embodiments, the intervention comprises behavioral intervention, which includes positive reinforcement of appropriate mealtime behaviors, bite persistence (e.g., contingency contacting, escape extinction, etc.), and stimulus fading; nutritional counseling; oral-motor therapy; and medical oversight to assure the treatment achieves a nutritionally complete diet, address potential skill deficits, and provide safeguards for potential organic concerns that may emerge during the course of treatment.

Upon completion of the intervention delivery process 600, the system proceeds to the patient discharge process 700 (further details of which will be explained in association with the description of FIG. 7). In various embodiments, the patient discharge process 700 is the process by which the patient is assigned a new intervention/treatment and/or the patient's intervention/treatment is generalized so that the patient does not relapse at a later date. Generally, if further treatment would be beneficial, the patient may be assigned to a new intervention (by returning to the patient assessment process 500). In one embodiment, generalization of the intervention comprises slowly transitioning the patient to eating in a setting outside the facility wherein the treatment was provided and training the caregiver to feed the patient in line with the methods used during the intervention. Once the patient discharge process 700 is complete, then the exemplary system process 300 ends thereafter.

Now referring to FIG. 4, an exemplary patient screening process 400 is shown according to one embodiment of the present disclosure. Generally, the patient screening process 400 is the process by which the system receives information from the caregiver regarding the patient's feeding behaviors. In various embodiments, the patient screening process 400 permits the system and/or the medical practitioner(s) to determine whether the patient is eligible for the treatment disclosed herein. In one embodiment, the patient screening process 400 comprises completion of a questionnaire/evaluation by the caregiver.

In various embodiments, the patient screening process 400 begins at step 402, wherein the system receives a patient referral. Generally, the patient referral may be a request from a caregiver to be considered for treatment, a referral from a medical provider of the patient, etc. Thus, at step 404, the system, in one embodiment, transmits the initial evaluation to the caregiver for completion. The initial evaluation, in various embodiments, comprises questions regarding the patient's feeding behaviors that permit the system and/or a medical provider to determine the patient's eligibility for treatment. For example, the initial evaluation may inquire as to feeding frequency and/or duration, foods eaten, food avoided, textures avoided, etc.

Generally, in one embodiment, treatment eligibility may be determined based on one or more of the following: (a) meeting diagnostic criteria for avoidant/restrictive food intake disorder ("ARFID") as evidenced by dependence on enteral feeding, oral nutritional formula supplementation, significant nutritional deficiency, and/or growth failure; (b) confirmed history of active and persistent mealtime behavioral difficulties (e.g., severe tantrums or disruptions when presented with food, etc.) measured by a psychologist; (c) medically cleared by a physician to proceed with an intervention focused on advancing the volume and/or variety of food; and (d) demonstrating minimal prerequisite oral motor skills (e.g., mid-blade elevation, jaw strength, lingual lateral pressure match or transverse tracking response to touch/pressure at lateral lingual border, etc.) required to support oral intake as determined by a non-nutritive oral motor evaluation conducted by a speech-language pathologist or occupational therapist. For some patients, the primary concern is food refusal, which is generally defined as dependence on formula either by enteral or oral formula supplementation (e.g., by bottle) for 50% or more of a child's caloric needs or failure to consume adequate intake to promote growth (e.g., faltering growth). For other patients, food refusal is the primary concern, which is generally defined as involving a limited variety of food consumed during meals. For yet other patients, severe food selectivity (e.g., complete rejection of one or more food groups—fruits, vegetables, proteins, grains, dairy; accepting five or fewer total food items; etc.) may be the primary qualifying concerns because these patients consumed enough volume to meet energy needs but have risk for nutrient inadequacies (e.g., scurvy, etc.) due to limited variety.

At step 406, the system determines whether the initial evaluation has been completed and returned by the caregiver. If the initial evaluation has not been completed and/or returned by the caregiver, then, in one embodiment at step 408, the system reminds the caregiver to complete and return the initial evaluation and returns to step 406. In various embodiments, the system may remove the patient from consideration if the initial evaluation is not returned promptly enough (e.g., after one week, two weeks, etc.), which could indicate that the caregiver will not give the treatment appropriate priority. If, however, the initial evaluation has been completed and returned, then, in one embodiment at step 410, the system generally determines the patient's feeding difficulty (e.g., the patient's feeding disorder(s) and feeding behaviors).

Depending on the severity of the patient's feeding difficulty, at step 412 in one embodiment, the system determines whether a referral is appropriate for the patient or if the patient should receive treatment through the system. Thus, at step 414 in one embodiment, if a referral is appropriate (e.g., because the patient's feeding difficulty is not severe enough to warrant treatment through the system, etc.), then the system retrieves preferred practitioner referrals and refers the patient to one or more of the preferred practitioners. If, however, a referral is not appropriate (e.g., because the patient's feeding difficulty is severe enough to warrant treatment through the system, etc.), then at step 416 in one embodiment, the system schedules an assessment of the patient. After steps 414 or 416, the exemplary patient screening process ends thereafter.

Referring now to FIG. 5, an exemplary patient assessment process 500 is shown according to one embodiment of the present disclosure. Generally, the patient assessment process 500 is the process by which the patient's feeding behaviors are assessed by one or more medical practitioners to develop an intervention for the patient. In one embodiment, wherein the patient's feeding disorder is less severe (but severe enough to potentially still warrant treatment), the patient assessment process 500 is only conducted by a single medical practitioner. In one embodiment, wherein the patient's feeding disorder is more severe, the patient assessment process 500 is conducted by multiple medical practitioners of varying expertise (e.g., behavioral psychologist, nutritionist, occupational therapist, speech therapist, gastroenterologist, social worker, etc.). The patient assessment process 500 may be conducted by observing a feeding of the patient by the caregiver in a location familiar to the patient (e.g., home, school, etc.).

In various embodiments, the patient assessment process 500 begins at step 502, wherein the system retrieves a patient file corresponding to a patient for whom an assessment has previously been scheduled (e.g., at step 416, from FIG. 4). Thus, at step 504 in various embodiments, the system determines the type of assessment to be conducted (e.g., single practitioner vs. multidisciplinary). Generally, the type of assessment may depend on the severity of the patient's feeding difficulty, with more severe feeding difficulties receiving multidisciplinary assessments and less severe feeding difficulties receiving single practitioner assessments.

At step 506, the assessment of the patient is conducted by the appropriate medical practitioners. In one embodiment, the assessment comprises an observation of the patient being fed by the caregiver in the home setting. Generally, the assessment is meant to serve as a baseline from which the appropriate intervention is determined. For example, data collected by feeding therapists during the assessment may comprise meal structure (e.g., food presented, meal duration, bite volume, food texture, utensils, seating, etc.), caregiver behaviors (e.g., instructions, prompts, consequences, etc.), and patient response to the presentation of food—focusing on both appropriate (e.g., acceptance, chewing, swallowing, grams consumed, etc.) and inappropriate (e.g., negative vocalizations, combined inappropriate behaviors, etc.) mealtime behaviors; feeding therapists may also identify potential reinforcers that can be utilized during intervention through a preference assessment protocol; dieticians may identify foods that will be targeted during intervention; oral-motor therapists may determine appropriate seating, utensils, and other therapeutic support based on the child's medical status; etc.

After the initial assessment has been completed, in various embodiments at step 508, the system determines whether additional assessment is necessary. For example, a single medical practitioner may have observed a feeding behavior that suggests a medical practitioner of a different discipline should also assess the patient. If additional assessment is appropriate, then in one embodiment at step 510, the additional assessment is conducted. After completing the additional assessment or if no additional assessment is required, the system proceeds, in one embodiment at step 512, to determine the appropriate intervention for the patient. The intervention may, in various embodiments, involve an intensive day treatment program that provides daily treatment to the patient in a specialized facility, an outpatient treatment program that provides weekly treatment to the patient in a specialized facility, or a referral to an outside provider that provides treatment to the patient as needed either in the outside provider's facility or the patient's home. Generally, the severity of the patient's feeding disorder determines which intervention is assigned to the patient (e.g., with the most severe feeding disorders being treated with the intensive day treatment program and the least severe feeding disorders being treated with a referral). Accordingly, at step 514 in various embodiments, the patient is assigned to the appropriate intervention and the exemplary patient assessment process 500 ends thereafter.

Now referring to FIG. 6, an exemplary intervention delivery process 600 is shown according to one embodiment of the present disclosure. Generally, the intervention delivery process 600 is the process by which the determined intervention is provided to the patient. The intervention delivered as part of the intervention delivery process 600 may, in various embodiments, involve an intensive day treatment program that provides daily treatment to the patient in a specialized facility or an outpatient treatment program that provides weekly treatment to the patient in a specialized facility. The intervention may generally be delivered by a single medical practitioner or a multidisciplinary team of medical practitioners.

In various embodiments, the intervention delivery process 600 begins at step 602, wherein the system determines the assigned intervention for the patient. Generally, the difference between the intensive day treatment program and the outpatient treatment program is the frequency of doses (also referred to herein as therapeutic activities) provided to the patient. For example, the intensive day treatment program may involve multiple treatment doses provided daily to the patient, whereas the outpatient treatment program may involve a single treatment dose delivered daily or even weekly to the patient.

Thus, at step 604 in one embodiment, the system determines the appropriate therapeutic activity/dose to provide to the patient and, at step 606, the appropriate therapeutic activity is conducted with/on the patient. For example, a patient may receive a treatment meal session, oral-motor therapy session, etc. In one embodiment, treatment meal sessions may occur in a private treatment room with an adjacent observation room. During a session, the subject sits in age-appropriate seating (e.g., highchair, booster seat, etc.), and the treatment room also contains a table, feeding utensils, small maroon spoons, massager brush, rubber-coated baby spoon, bib, serving tray, and/or a scale with an intake log. A session may generally target a total of 16 foods items (e.g., four fruits, four vegetables, four starches, and four meats) plus a nutritionally complete drink. The feeding therapist may randomly select one food from each group and randomly present these four foods at a designated texture (e.g., puree, etc.) and bite volume (e.g., half-level bolus size, 0.2 cm$^3$, 1 cm$^3$, 2 cm$^3$, 3 cm$^3$, etc.). Generally, the order of food item presentation remains the same within a given session. In other sessions, the selection of foods may not comprise one food from each group but may instead comprise only foods from the same group, may comprise two foods from only two groups, etc.

At step 608, in various embodiments, the patient's response to the therapeutic activity is recorded. In one embodiment, the response may be recorded only once per therapeutic activity (and steps 608-618 are conducted only once per therapeutic activity). In another embodiment, the response may be recorded throughout the therapeutic activity (and steps 608-618 are conducted throughout the therapeutic activity). For example, treatment meal sessions are generally structured based on protocols that specify the feeder behavior (e.g., verbal instructions, prompts, social attention, etc.), format of bite presentations (e.g., volume and variety of food presented, etc.), level of persistence with mealtime demands (e.g., non-removal of the plate, non-removal of the spoon, etc.), and consequences for appropriate (e.g., positive) and inappropriate (e.g., negative) mealtime behaviors (e.g., access to a toy or other preferred item, etc.). Different treatment elements are introduced into the intervention based on a patient's pattern of behavior during meals, which is monitored on a bite-by-bite basis. In one embodiment, a smart spoon, coated with a pleasing texture, may be used for the treatment meal sessions, wherein the spoon records the amount of food fed to the patient. In one embodiment, a standardized spoon volume (e.g., ¼ level spoon, ½ level spoon, etc.), delivering therapeutic foods by type and texture, may be used for the treatment meal sessions, wherein the feeder records the amount of food fed to the patient. In one embodiment, the amount of food fed to the patient may be determined by comparing the weight of prepared food before a meal session to the weight of all off remaining after a meal session. In one embodiment, the patient's response to the food may be recorded (e.g., acceptance, disruption, and grams of food consumed) such that acceptance is recorded when at least half of the feeding utensil enters the patient's mouth and disruption is recorded when the patient rejects the feeding utensil by turning its head away from the feeding utensil, pushing away the feeding utensil, or pushing away a hand of the feeder holding the feeding utensil.

Generally, at steps 610 and 612, the patient's response is analyzed to determine whether the appropriate progress is being made. Appropriate progress may be determined based on the age of the patient and/or severity of the feeding disorder. For example, if a patient is starting to eat the appropriate amount of food for his/her age/weight, then appropriate progress is being made. In one embodiment, this level of progress permits markers of success—such as the case involving tube weaning or discontinuation of supplemental formula feedings. Similarly, if the patient is increasing the number of foods and/or food textures eaten, then appropriate progress is being made. Generally, however, if appropriate progress is not being made, then in one embodiment at step 614, the assessment criteria (used as part of the patient assessment process 500) are optionally modified so that similar patients are not assigned to similar interventions in the future. If, in contrast, appropriate progress is being made, then in one embodiment at step 616, the next appropriate action is taken. For example, if the patient accepts the food, then the food may be presented to the patient again. If, however, a disruption is recorded, then a different food may be selected and presented to the patient. Generally, a treatment meal session may not end until all of the different food items have been presented to the patient. Further, for example, the foods introduced in the next treatment meal session may be changed; a new oral-motor therapy session may be conducted; etc. In one embodiment, the next appropriate action may be waiting until the next day to conduct the next session/therapeutic activity, etc.

After taking the appropriate action or modifying the assessment criteria, in various embodiments at step 618, the system determines whether additional therapeutic activity is to be conducted. In one embodiment, the patient may be scheduled to receive multiple therapeutic activities a day (or over several days). For example, a patient may each day receive a predetermined number of treatment meal sessions (e.g., 2, 3, 4, 5, 6, etc.) of a predetermined length (e.g., 10 minutes, 15, 20, 25, 30, 40, etc.), wherein meal sessions may generally be spaced to provide adequate time for digestion to occur, with potentially long breaks between lunch and dinner for small children to nap, etc. Thus, if additional therapeutic activity is to be conducted (either that day or on another day), then, in one embodiment the system returns to step 604 to determine the appropriate therapeutic activity. If, however, no additional therapeutic activity is to be performed and the patient is ready for discharge, then the exemplary intervention delivery process 600 ends thereafter.

Referring now to FIG. 7, an exemplary patient discharge process 700 is shown according to one embodiment of the present disclosure. Generally, the patient discharge process 700 is the process by which the patient is assigned a new intervention and/or the patient's intervention is generalized so that the patient does not relapse at a later date. Generally, if further treatment would be beneficial, the patient may be assigned to a new intervention (by returning to the patient assessment process 500). In one embodiment, generalization of the intervention comprises slowly transitioning the patient to eating in a setting outside the facility wherein the treatment was provided and training the caregiver to feed the patient in line with the methods used during the intervention.

In various embodiments, the patient discharge process 700 begins at step 702, wherein the system retrieves a patient file corresponding to a patient for whom the intervention delivery process 600 has already been completed. Thus, at step 704 in one embodiment, the system determines whether additional intervention would be appropriate for that patient. For example, the patient may have made enough progress to move from the intensive day treatment program to the outpatient treatment program or the patient may have regressed such that moving from the outpatient treatment program to the intensive day treatment program is appropriate. If additional intervention is appropriate, then the system returns to the patient assessment process 500 to determine the additional intervention.

If, however, additional intervention is not appropriate, then the system proceeds to step 706, wherein in one embodiment the caregiver is trained to feed the patient in line with the intervention to prevent relapse. For example, the caregiver may be trained how to prepare food for the patient, how to feed the patient, how to respond to negative feeding behaviors from the patient, how to introduce new foods/textures to the patient, etc. Once the caregiver has been trained, then, at step 708, the intervention is generalized such that the caregiver gradually begins feeding the patient at home (e.g., one meal a day or every other day, increasing until the patient is receiving all meals outside of the treatment setting/facility). In one embodiment, the medical practitioner may visit the home to assist with intervention generalization. In one embodiment, the medical practitioner may feed the patient in the home. Generally, after conducting the intervention generalization, the system proceeds, at step 710 in one embodiment, to complete the discharge plan corresponding to the patient. The discharge plan, in various embodiments, outlines the outpatient support, as identified by the treatment team, that may be necessary to maintain and/or extend the gains made during the treatment process. Thus, after completing the discharge plan, the exemplary patient discharge process 700 ends thereafter.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A system for treating one or more feeding disorders in a human to improve one or more feeding behaviors of the human, comprising:
    a caregiver electronic computing device that generates an evaluation regarding the feeding disorders of the human and transmits the evaluation to a feeding management system;
    the feeding management system that receives the evaluation from the caregiver electronic computing device and determines the one or more feeding orders to be treated and, based on the one or more feeding orders, transmits a request to a practitioner electronic computing device for an assessment of the one or more feeding behaviors of the human;
    the practitioner electronic computing device that receives the request for the assessment from the feeding management system, generates the assessment, and transmits the assessment to the feeding management system;
    the feeding management system that receives the assessment from the practitioner electronic computing device and determines, based on a comparison of the evaluation and the assessment with one or more predefined rules, an intervention that will treat the one or more feeding disorders and will improve the one or more feeding behaviors of the human, wherein the determined intervention comprises a meal session during which a bite of food is presented by a feeder using a feeding utensil and a response of the human to the bite of food is recorded using the practitioner electronic computing device;
    the practitioner electronic computing device that receives the response and transmits the response to the feeding management system; and
    the feeding management system that:
        receives the response from the practitioner electronic computing device;
        determines, based on the response, whether to conduct an additional intervention, wherein an additional intervention is appropriate if the response does not demonstrate an improvement in the one or more feeding behaviors that meets a predetermined threshold; and
        upon determining not to conduct the additional intervention, provides an instruction to discharge the human.

2. The system of claim 1, wherein the one or more feeding disorders are selected from a list comprising food refusal and food selectivity.

3. The system of claim 1, wherein the one or more feeding behaviors of the human are selected from a list comprising choking, gagging, vomiting, difficulty swallowing, oral-motor deficiencies, and tantrums.

4. The system of claim 1, wherein the feeding management system:
prior to determining not to conduct the additional intervention, determines to conduct the additional intervention;
upon determining to conduct the additional intervention, conducts an additional meal session;
receives a recorded result of the additional meal session from the practitioner electronic computing device; and
determines, based on the recorded result and the recorded response, whether to conduct the determined intervention again.

5. The system of claim 4, wherein the recorded response and the recorded result are selected from a list comprising acceptance, disruption, and grams of food consumed.

6. The system of claim 5, wherein acceptance is recorded when at least half of the feeding utensil enters the human's mouth.

7. The system of claim 5, wherein disruption is recorded when the human rejects the feeding utensil by turning its head away from the feeding utensil, pushing away the feeding utensil, or pushing away a hand of the feeder holding the feeding utensil.

8. The system of claim 5, wherein the additional meal session further comprises:
a) presenting to the human a first bite of a first food selected from a menu of food based on the one or more feeding disorders and the one or more feeding behaviors;
b) based on the human's acceptance or disruption, either presenting the first bite another time or presenting a first bite of a different food selected from the menu of food; and
c) repeating step b until at least one bite of each of the foods from the menu of food has been presented to the human.

9. The system of claim 8, wherein the first bite of the first food is a volume of food from about 0.2 $cm^3$ to about 3.0 $cm^3$.

10. The system of claim 9, wherein the volume of food is increased when the rate of the human accepting the first bite is higher than a previous rate or is stable.

11. The system of claim 10, wherein the first food is pureed.

12. The system of claim 11, wherein the predetermined threshold comprises consuming a predetermined number of grams, based on the age of the human, of each of the foods from the menu of food.

* * * * *